United States Patent [19]

Ueda et al.

[11] Patent Number: 4,540,692
[45] Date of Patent: Sep. 10, 1985

[54] ANTI-INFLAMMATORY N-(1-OXO-2,4,6-CYCLOHEPTATRIENYL)2H-1,2-BENZOTHIAZINE-3-CARBOXAMIDE 1,1-DIOXIDE DERIVATIVES, COMPOSITIONS, AND METHOD OF USE

[75] Inventors: Ikuo Ueda, Toyonaka; Masayuki Kato, Minoo; Yoshiharu Kasai, Daito, all of Japan

[73] Assignee: Fujisawa Pharmaceutical Co., Ltd., Osaka, Japan

[21] Appl. No.: 589,338

[22] Filed: Mar. 14, 1984

[30] Foreign Application Priority Data

Mar. 31, 1983 [JP] Japan .................................. 58-57071

[51] Int. Cl.$^3$ ..................... A61K 31/54; C07D 279/02
[52] U.S. Cl. ........................................ 514/225; 544/49
[58] Field of Search .......................... 544/49; 424/246; 514/225

[56] References Cited

U.S. PATENT DOCUMENTS

| | | | |
|---|---|---|---|
| 3,591,584 | 7/1971 | Lombardino | 544/49 |
| 3,862,319 | 1/1975 | Lombardino et al. | 544/49 |

FOREIGN PATENT DOCUMENTS

| | | | |
|---|---|---|---|
| 1943265 | 8/1970 | Fed. Rep. of Germany | 544/49 |
| 57-70888 | 5/1982 | Japan | 544/49 |

OTHER PUBLICATIONS

Chemical Abstracts, 76, (1972), Lombardino et al., "Synthesis and Antiinflammatory Activity of Some 3-Carboxamides of . . . ", p. 28.

*Primary Examiner*—Henry R. Jiles
*Assistant Examiner*—J. G. Mullins
*Attorney, Agent, or Firm*—Oblon, Fisher, Spivak, McClelland & Maier

[57] ABSTRACT

The invention relates to novel tropone derivatives, of antiinflammatory, analgesic and antirheumatic activity, of the formula:

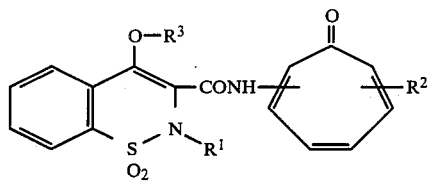

wherein
$R^1$ is hydrogen or lower alkyl,
$R^2$ is hydrogen, hydroxy, halogen, lower alkyl, or lower alkoxy, and
$R^3$ is hydrogen or acyl,
and pharmaceutically acceptable salts thereof.

10 Claims, No Drawings

ANTI-INFLAMMATORY N-(1-OXO-2,4,6-CYCLOHEPTATRIENYL)2H-1,2-BENZOTHIAZINE-3-CARBOXAMIDE 1,1-DIOXIDE DERIVATIVES, COMPOSITIONS, AND METHOD OF USE

The present invention relates to novel tropone derivatives. More particularly, it relates to novel tropone derivatives which have antiinflammatory, analgesic and antirheumatic activities, to process for preparation thereof, to pharmaceutical composition comprising the same, and to methods of using the same therapeutically in the treatment of inflammation, various pains and rheumatism in human being and animals.

Accordingly, one object of this invention is to provide novel tropone derivatives which are useful as antiinflammatory, analgesic and antirheumatic agents.

Another object of this invention is to provide a process for preparation of said tropone derivatives.

A further object of this invention is to provide pharmaceutical composition comprising, as an active ingredient, said tropone derivative.

Still further object of this invention is to provide a method of using said tropone derivatives in the treatment of inflammation, various pains and rheumatism in human being and animals.

Some thiazine derivatives having antiinflammatory activity have been known as described, for example, in U.S. Pat. No. 3,591,584.

The object tropone derivatives are novel and can be represented by the following general formula [I].

wherein
$R^1$ is hydrogen or lower alkyl,
$R^2$ is hydrogen, hydroxy, halogen, lower alkyl or lower alkoxy, and
$R^3$ is hydrogen or acyl.

As to the object compound [I], the following points are to be noted. That is, when $R^3$ is hydrogen, the object compound can be alternatively represented by its tautomers as shown in the following.

wherein $R^1$ and $R^2$ are each as defined above.

In the present specification and claim, however, the object compound of this invention is represented by the formula (A) only for the convenient sake.

The object compound [I] and its salt can be prepared by the following processes.

-continued

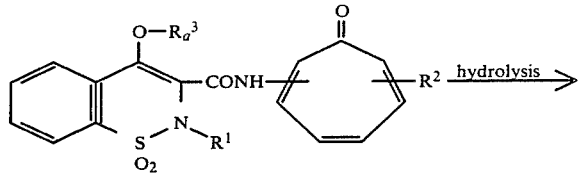

or its salt [Ib]

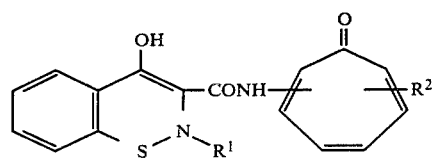

or its salt [Ia]

wherein
R[1], R[2] and R[3] are each as defined above, and $R_a^3$ is acyl.

In the above and subsequent description of the present specification, suitable examples and illustrations for the various definitions to be included within the scope of the invention are explained in detail as follows:

The term "lower" is intended to mean a group having 1 to 6 carbon atom(s), unless otherwise provided.

Suitable examples of lower alkyl for R[1] and R[2] may be a straight or branched one such as methyl, ethyl, propyl, isopropyl, butyl, isobutyl, t-butyl, pentyl, hexyl or the like.

Suitable examples of lower alkoxy for R[2] may be methoxy, ethoxy, propoxy, isopropoxy, butoxy, t-butoxy, pentyloxy, hexyloxy or the like.

Suitable examples of halogen for R[2] include chlorine, bromine, iodine and fluorine.

Suitable examples of acyl for R[3] and $R_a^3$ may be lower alkanoyl [e.g. formyl, acetyl, propionyl, hexanoyl, etc.], aroyl [e.g. benzoyl, naphthoyl, etc.], ar(lower)alkenoyl [e.g. cinnamoyl, etc.] or the like.

Suitable pharmaceutically acceptable salts of the object compound [I] are conventional non-toxic salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], and the like.

The processes for preparing an object compound [I] and its salt is explained in detail in the following.

Process 1

The object compound [I] and its salt can be prepared by reacting a compound [II] or its reactive derivative at the carboxy group or a salt thereof with a compound [III] or its reactive derivative at the amino group or a salt thereof.

Suitable reactive derivatives at the carboxy group of the compound [II] may include an acid halide, an acid anhydride, an ester, an activated amide and the like.

Suitable examples of such reactive derivatives may be an ester such as lower alkyl ester [e.g. methyl ester, ethyl ester, propyl ester, hexyl ester, etc.] or an activated ester with N-hydroxysuccinimide, N-hydroxyphthalimide or 1-hydroxy-6-chlorobenzotriazole, an acid chloride, an acid azide, a mixed acid anhydride with an acid such as substituted phosphoric acid [e.g. dialkylphosphoric acid, phenylphosphoric acid, etc.], aliphatic carboxylic acid [e.g. pivalic acid, acetic acid, trichloroacetic acid, etc.] or the like, a symmetrical acid anhydride, an activated amide with imidazole, triazole or dimethylpyrazole, or the like.

Suitable reactive derivatives at the amino group of the compound [III] include conventional ones used in amidation, for example, Schiff's base type imino or its tautomeric enamine type isomer formed by reaction of the compound [III] with a carbonyl compound, a silyl derivative formed by reaction of the compound [III] with a silyl compound such as trimethylsilylacetamide, bis(trimethylsilyl)acetamide or the like, a derivative formed by reaction of the compound [III] with phosphorus trichloride or phosgene, and the like.

The reactive derivatives of the compounds [II] and [III] can be selected according to the kinds of the compounds [II] and [III], respectively.

Suitable salts of the compound [II] and its reactive derivative at the carboxy group may be the same as those exemplified for the compound [I], and suitable salts of the compound [III] and its reactive derivative at the amino group may include a conventional base addition salt as exemplified for the compound [I] and a conventional acid addition salt [e.g. hydrochloride, hydrobromide, formate, acetate, benzenesulfonate, etc.].

When the compound [II] is used in a free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-ethyl-N'-(3-dimethylaminopropyl)carbodiimide, thionyl chloride, oxalyl chloride, lower alkoxycarbonyl halide [e.g. ethyl chloroformate, isobutyl chloroformate, etc.], 1-(p-chlorobenzenesulfonyloxy)-6-chloro-1H-benzotriazole, or the like.

The reaction is usually carried out in a conventional solvent such as water, acetone, dioxane, chloroform, methylene chloride, ethylene chloride, tetrahydrofuran, benzene, toluene, ethyl acetate, N,N-dimethylformamide, pyridine or any other organic solvent which does not adversely influence the reaction. Among these solvents, hydrophilic solvents may be used in a mixture with water.

The reaction may be preferably carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], tri(lower)alkylamine [e.g. trimethylamine, triethylamine, etc.], pyridine or its derivative [e.g. picoline, lutidine, 4-dimethylaminopyridine, etc.], or the like. In case that the base or the condensing agent to be used is liquid, it can also be used as a solvent.

Further, when the compound [III] contains a hydroxy group, the reaction is preferably conducted in an inert atmosphere such as a stream of nitrogen gas.

The reaction temperature is not critical, and the reaction is usually carried out under cooling, at ambient temperature or under warming or heating.

Process 2

The object compound [Ib] and its salt can be prepared by reacting a compound [Ia] or its salt with a compound

[IV] or its reactive derivative at the carboxy group or a salt thereof.

Suitable reactive derivatives at the carboxy group of the compound [IV] may be the same as those exemplified for the compound [II].

Suitable salts of the compound [IV] may be the same as those exemplified for the compound [I].

This reaction can be carried out substantially in the same manner as that of Process 1, and therefore the reaction mode and reaction conditions [e.g. condensing agent, base, solvent, reaction temperature, etc.] of this process are to be referred to those as explained in Process 1.

Process 3

The object compound [Ia] and its salt can be prepared by hydrolyzing the compound [Ib] or its salt.

This reaction is usually carried out in the presence of an acid or a base.

Suitable acid includes an inorganic acid [e.g. hydrochloric acid, hydrobromic acid, sulfuric acid, etc.], an organic acid [e.g. formic acid, acetic acid, trifluoroacetic acid, propionic acid, benzenesulfonic acid, p-toluenesulfonic acid, etc.], an acidic ion exchange resin and the like.

Suitable base includes an inorganic base such as alkali or alkaline earth metal hydroxide or the corresponding carbonate or bicarbonate [e.g. sodium hydroxide, potassium hydroxide, sodium carbonate, potassium carbonate, lithium carbonate, sodium bicarbonate, calcium hydroxide, magnesium hydroxide, etc.], ammonium hydroxide or the like; an organic base such as an alkoxide or phenoxide of the above metal [e.g. sodium ethoxide, sodium methoxide, lithium phenoxide, etc.], an amine such as mono-, di- or trialkylamine [e.g. methylamine, ethylamine, propylamine, isopropylamine, butylamine, N,N'-dimethyl-1,3-propanediamine, trimethylamine, triethylamine, etc.], unsubstituted, mono- or disubstituted arylamine [e.g. aniline, N-methylaniline, N,N-dimethylaniline, etc.], a heterocyclic base [e.g. pyrrolidine, morpholine, N-methylmorpholine, N-methylpiperidine, N,N'-dimethylpiperazine, pyridine, etc.], hydrazines [e.g. hydrazine, methylhydrazine, ethylhydrazine, etc.] or the like; a basic ion-exchange resin and the like.

This reaction is usually carried out in a solvent which does not adversely influence the reaction such as water, hydrophilic solvent such as alcohol [e.g. methanol, ethanol, propanol, etc.], acetone, N,N-dimethylformamide, tetrahydrofuran, dioxane, dimethyl sulfoxide, etc. or a mixture thereof, and other hydrophobic solvent such as benzene, diethyl ether, etc. may also be used as a solvent. In case that the acid or base to be used in this reaction is liquid, it can also be used as a solvent.

The reaction temperature is not critical, and the reaction is usually carried out at ambient temperature or under warming or heating.

The new tropone derivatives [I] and pharmaceutically acceptable salts thereof possess antiinflammatory, analgesic and antirheumatic activities, and are useful for a therapeutic treatment of inflammation, various pains [e.g. headache, toothache, menorrhalgia, etc.] and rheumatism.

For therapeutic purpose, the compounds according to the present invention can be used in a form of pharmaceutical preparation containing one of said compounds, as an active ingredient, in admixture with a pharmaceutically acceptable carrier such as an organic or inorganic solid or liquid excipient suitable for oral or parenteral administration. The pharmaceutical preparations may be capsules, tablets, dragees, granules, solution, suspension, emulsion, or the like. If desired, there may be included in the above preparations, auxiliary substances, stabilizing agents, wetting or emulsifying agents, buffers and other commonly used additives.

While the dosage of the compounds will vary depending upon the age and condition of the patient, an average single dose of about 0.1 mg, 1 mg, 10 mg, 50 mg, 100 mg, 250 mg, 500 mg and 1000 mg of the compounds according to the present invention may be effective for treating inflammation, various pains and rheumatism. In general, amounts between 0.1 mg/body and about 1,000 mg/body or even more may be administered per day.

In order to illustrate the usefulness of the object compound [I], the pharmacological test data of the representative compound of the object compounds [I] are shown below.

Carrageenin edema test

Five Sprague-Dawley rats were fasted for 24 hours and submitted to the study. First, 0.1 ml of carrageenin (1%) was subcutaneously injected into the paw of the right hind limb and after 3 hours the rat was sacrificed. The untreated limb and the edematous limb were respectively incised off at the junction of the tibia and weighed. The difference in weight between the edematous limb and the untreated limb was taken as the weight of the edema.

The test compound was orally administered 60 minutes prior to the administration of carrageenin and the swelling in the treated limb was compared with that in the control limb. The test compound was administered in a dose of 10 mg/kg.

| Test compound (Example No.) | % Inhibition of carrageenin edema |
| --- | --- |
| Example 1 | 51.4 |

The following examples are given only for the purpose of illustrating the present invention in more detail.

EXAMPLE 1

A solution of methyl 4-hydroxy-2-methyl-2H-1,2-benzothiazine-3-carboxylate 1,1-dioxide (3.0 g) and 2-amino-2,4,6-cycloheptatrien-1-one (1.6 g) in xylene (100 ml) is refluxed for 8 hours. The reaction mixture is then allowed to stand at room temperature for 15 hours. The crystals that have separated out are collected by filtration, washed with toluene and recrystallized from dimethylformamide to give 4-hydroxy-2-methyl-N-(1-oxo-2,4,6-cycloheptatrien-2-yl)-2H-1,2-benzothiazine-3-carboxamide 1,1-dioxide (0.68 g), m.p. 259°–261° C.

IR (Nujol): 3220, 1615, 1590, 1560, 1505, 1495 cm$^{-1}$
NMR (DMSO-d$_6$, δ): 2.93 (3H, s), 7.17–8.13 (7H, m), 8.93 (2H, d, J=9 Hz), 10.63 (1H, brs)
Elemental analysis: Calcd. for $C_{17}H_{14}N_2O_5S$: C, 56.97; H, 3.94; N, 7.82: Found: C, 57.01; H, 3.90; N, 7.95.

EXAMPLE 2

In a nitrogen atmosphere, a solution of methyl 4-hydroxy-2-methyl-2H-1,2-benzothiazine-3-carboxylate 1,1-dioxide (0.54 g) and 5-amino-2-hydroxy-2,4,6-cycloheptatrien-1-one (0.33 g) in xylene (15 ml) is refluxed for 7.5 hours. The reaction mixture is then allowed to stand at room temperature overnight. The crystals that have separated out are collected by filtration and recrystallized from dimethylformamide-methanol to give 4-hydroxy-2-methyl-N-(2-hydroxy-1-oxo-2,4,6-cycloheptatrien-5-yl)-2H-1,2-benzothiazine-3-carboxamide 1,1-dioxide (0.4 g), m.p. 258°–265° C.

IR (Nujol): 3300, 1660, 1605, 1520 cm$^{-1}$

NMR (DMSO-d$_6$, δ): 2.90 (3H, s), 7.30 (2H, d, J=12 Hz), 7.73 (2H, d, J=12 Hz), 7.90–8.37 (4H, m), 10.50 (1H, s)

Elemental analysis: Calcd. for $C_{17}H_{14}N_2O_6S$: C, 54.54; H, 3.77; N, 7.48: Found: C, 54.47; H, 3.74; N, 7.55.

EXAMPLE 3

A solution of methyl 4-hydroxy-2-methyl-2H-1,2-benzothiazine-3-carboxylate 1,1-dioxide (2.4 g) and 2-amino-4-methyl-2,4,6-cycloheptatrien-1-one (1.3 g) in xylene (50 ml) is refluxed for 7 hours. The reaction mixture is then allowed to stand at room temperature overnight. The resulting crystals (1.0 g) are collected by filtration and recrystallized from dioxane to give 4-hydroxy-2-methyl-N-(4-methyl-1-oxo-2,4,6-cycloheptatrien-2-yl)-2H-1,2-benzothiazine-3-carboxamide 1,1-dioxide (0.8 g), m.p. 235°–242° C.

IR (Nujol): 3260, 1650, 1615, 1600, 1560, 1500 cm$^{-1}$

NMR (CF$_3$COOH, δ): 3.00 (3H, s), 3.12 (3H, s), 7.50–8.50 (8H, m)

Elemental analysis: Calcd. for $C_{18}H_{16}N_2O_5S$: C, 58.05; H, 4.33; N, 7.52: Found: C, 57.93; H, 4.56; N, 7.51.

EXAMPLE 4

A solution of methyl 4-hydroxy-2-methyl-2H-1,2-benzothiazine-3-carboxylate 1,1-dioxide (1.2 g) and 2-amino-6-methyl-2,4,6-cycloheptatrien-1-one (0.7 g) in xylene (21 ml) is refluxed for 8 hours. The reaction mixture is then allowed to stand at room temperature for 2 days. The crystals that have separated out are collected by filtration, washed with toluene and recrystallized from dimethylformamide to give 4-hydroxy-2-methyl-N-(6-methyl-1-oxo-2,4,6-cycloheptatrien-2-yl)-2H-1,2-benzothiazine-3-carboxamide 1,1-dioxide (0.8 g), m.p. 276°–280° C.

IR (Nujol): 3240, 1625, 1600, 1555, 1510 cm$^{-1}$

NMR (CF$_3$CO$_2$H, δ): 3.0 (3H, s), 3.17 (3H, s), 7.8–8.7 (8H, m)

Elemental analysis: Calcd. for $C_{18}H_{16}N_2O_5S$: C, 58.05; H, 4.33; N, 7.52: Found: C, 57.85; H, 4.22; N, 7.52.

EXAMPLE 5

A solution of methyl 4-hydroxy-2-methyl-2H-1,2-benzothiazine-3-carboxylate 1,1-dioxide (1.5 g) and 2-amino-7-methoxy-2,4,6-cycloheptatrien-1-one (0.8 g) in xylene (25 ml) is refluxed for 6.5 hours. The reaction mixture is then allowed to stand at room temperature overnight. The crystals that have separated out are collected by filtration and recrystallized from dimethylformamide to give 4-hydroxy-2-methyl-N-(7-methoxy-1-oxo-2,4,6-cycloheptatrien-2-yl)-2H-1,2 -benzothiazine-3-carboxamide 1,1-dioxide (0.7 g), m.p. 243°–247° C.

IR (Nujol); 3150, 1640, 1565, 1520 cm$^{-1}$

NMR (DMSO-d$_6$, δ): 2.93 (3H, s), 3.97 (3H, s), 7.16–7.50 (3H, m), 7.76–8.13 (4H, m), 8.83–9.10 (1H, m), 10.62 (1H, s)

Elemental analysis: Calcd. for $C_{18}H_{16}N_2O_6S$: C, 55.66; H, 4.15; N, 7.21: Found: C, 55.71; H, 4.28; N, 7.18.

EXAMPLE 6

In a nitrogen atmosphere, a solution of methyl 4-hydroxy-2-methyl-2H-1,2-benzothiazine-3-carboxylate 1,1-dioxide (4.0 g) and 5-amino-2-methoxy-2,4,6-cycloheptatrien-1-one (2.7 g) in xylene (100 ml) is refluxed for 6 hours. The reaction mixture is then allowed to stand at room temperature overnight. The crystals that have separated out are collected by filtration and purified by silica gel (40 g) column chromatography using methanol-dichloromethane (5:95) as the eluent. The resulting crude product is recrystallized from dioxane-methanol to give 4-hydroxy-2-methyl-N-(2-methoxy-1-oxo-2,4,6-cycloheptatrien-5-yl)-2H-1,2-benzothiazine-3-carboxamide 1,1-dioxide (0.3 g), m.p. 215°–218° C.

IR (Nujol): 3250, 1635, 1590, 1530 cm$^{-1}$

NMR (DMSO-d$_6$, δ): 2.90 (3H, s), 3.90 (3H, s), 6.90–8.30 (8H, m), 10.47 (1H, s)

EXAMPLE 7

A mixture of methyl 4-hydroxy-2-methyl-2H-1,2-benzothiazine-3-carboxylate 1,1-dioxide (0.65 g) and 2-amino-5-hydroxy-2,4,6-cycloheptatrien-1-one (0.40 g) in xylene (12 ml) was refluxed for 48 hours. The reaction mixture was cooled to room temperature. The crystals were collected by filtration and washed successively with methanol, water and methanol to give 4-hydroxy-N-(5-hydroxy-1-oxo-2,4,6-cycloheptatrien-2-yl)-2-methyl-2H-1,2-benzothiazine-3-carboxamide 1,1-dioxide (0.4 g).

m.p. 270°–275° C.

IR (Nujol) : 3230, 1605, 1500, 1215, 870 cm$^{-1}$

NMR (NaOD-D$_2$O, δ) : 2.80 (3H, s), 6.63 (1H, dd, J=2,12 Hz), 7.0–8.3 (7H, m), 8.5 (1H, d, J=12 Hz)

Elemental analysis Calcd. for $C_{17}H_{14}N_2O_6S$: C, 54.54; H, 3.77; N, 7.48: Found: C, 54.06; H, 3.90; N, 7.29.

EXAMPLE 8

A mixture of methyl 4-hydroxy-2-methyl-2H-1,2-benzothiazine-3-carboxylate 1,1-dioxide (1.5 g) and 2-amino-5-chloro-2,4,6-cycloheptatrien-1-one (0.87 g) in xylene (37 ml) was refluxed for 24 hours. The reaction mixture was cooled to room temperature. The crystals were collected by filtration and recrystallized from N,N-dimethylformamide to give N-(5-chloro-1-oxo-2,4,6-cycloheptatrien-2-yl)-4-hydroxy-2-methyl-2H-1,2-benzothiazine-3-carboxamide 1,1-dioxide (0.89 g).

m.p. 250° C. (dec.)

IR (Nujol) : 3250, 1650, 1620, 1600, 1570, 1560 cm$^{-1}$

Elemental analysis Calcd. for $C_{17}H_{13}ClN_2O_5S$: C, 51.98; H, 3.34; N, 7.13: Found: C, 51.68; H, 3.28; N, 7.11.

EXAMPLE 9

A mixture of methyl 4-hydroxy-2-methyl-2H-1,2-benzothiazine-3-carboxylate 1,1-dioxide (2.95 g) and 2-amino-7-hydroxy-2,4,6-cycloheptatrien-1-one (1.5 g) in xylene (103 ml) was refluxed for 52 hours. The reaction mixture was cooled to room temperature. The crystals were collected by filtration and washed successively with N,N-dimethylformamide and chloroform to give 4-hydroxy-N-(7-hydroxy-1-oxo-2,4,6-cycloheptatrien-2-yl)-2-methyl-2H-1,2-benzothiazine-3-carboxamide 1,1-dioxide (3.7 g).

m.p. 294°–296° C.

IR (Nujol) : 3300, 3270, 3060, 1630, 1610, 1595, 1520 cm$^{-1}$

NMR (NaOD-D$_2$O, δ) : 2.83 (3H, s), 6.7–7.2 (5H, m), 8.0–8.3 (2H, m), 8.5–8.8 (2H, m)

Elemental analysis Calcd. for C$_{17}$H$_{14}$N$_2$O$_6$S: C, 54.54; H, 3.77; N, 7.48: Found: C, 54.41; H, 3.78; N, 7.51.

EXAMPLE 10

A mixture of methyl 4-hydroxy-2-methyl-2H-1,2-benzothiazine-3-carboxylate 1,1-dioxide (0.36 g) and 2-amino-5-methoxy-2,4,6-cycloheptatrien-1-one (0.20 g) in xylene (9 ml) was refluxed for 40 hours. The reaction mixture was cooled to room temperature. The crystals were collected by filtration and washed with xylene to give 4-hydroxy-N-(5-methoxy-1-oxo-2,4,6-cycloheptatrien-2-yl)-2-methyl-2H-1,2-benzothiazine-3-carboxamide 1,1-dioxide (0.45 g).

m.p. 251°–253° C.

IR (Nujol) : 3300, 3150, 1610, 1595, 1560, 1500 cm$^{-1}$

NMR (DMSO-d$_6$, δ) : 2.93 (3H, s), 3.87 (3H, s), 6.7–8.3 (7H, m), 8.83 (1H, d, J=12 Hz), 10.15 (1H, m).

Elemental analysis Calcd. for C$_{18}$H$_{16}$N$_2$O$_6$S: C, 55.66; H, 4.15; N, 7.21: Found: C, 56.04; H, 4.22; N, 7.27.

EXAMPLE 11

To a mixture of 4-hydroxy-2-methyl-N-(1-oxo-2,4,6-cycloheptatrien-2-yl)-2H-1,2-benzothiazine-3-carboxamide 1,1-dioxide (2.0 g) and cinnamoyl chloride (1.3 g) in N,N-dimethylformamide (30 ml) was added pyridine (0.9 ml). The mixture was stirred at room temperature for 2.5 hours. The reaction mixture was poured into cooled water to give crystals, which were collected by filtration and washed with water. The crude crystals were dissolved in chloroform and the solution was washed successively with water and brine, dried over anhydrous magnesium sulfate, treated with activated charcoal and evaporated under reduced pressure to give crystals. The crystals were recrystallized from a mixture of ethyl acetate and hexane to give N-(1-oxo-2,4,6-cycloheptatrien-2-yl)-2-methyl-4-cinnamoyloxy-2H-1,2-benzothiazine-3-carboxamide 1,1-dioxide (2.4 g).

m.p. 181°–184° C.

IR (Nujol) : 3280, 1755, 1678, 1635, 1618, 1590, 1550, 1490 cm$^{-1}$

NMR (DMSO-d$_6$, δ) : 3.06 (3H, s), 6.96 (1H, d, J=16 Hz), 7.0–8.2 (13H, m), 8.90 (1H, d, J=9 Hz), 10.63 (1H, s)

EXAMPLE 12

To a suspension of N-(1-oxo-2,4,6-cycloheptatrien-2-yl)-2-methyl-4-cinnamoyloxy-2H-1,2-benzothiazine-3-carboxamide 1,1-dioxide (0.5 g) in methanol (50 ml) was added dropwise 1N sodium hydroxide solution (1.5 ml) at room temperature. The mixture was stirred for 8 hours at room temperature and then neutralized with 1N hydrochloric acid. The mixture was evaporated under reduced pressure and the residue was washed with water and dried to give crystals, which were recrystallized from N,N-dimethylformamide to give 4-hydroxy-2-methyl-N-(1-oxo-2,4,6-cycloheptatrien-2-yl)-2H-1,2-benzothiazine-3-carboxamide 1,1-dioxide (0.1 g).

m.p. 259°–261° C.

IR (Nujol) : 3220, 1615, 1590, 1560, 1505, 1495 cm$^{-1}$

NMR (DMSO-d$_6$, δ) : 2.93 (3H, s), 7.17–8.13 (7H, m), 8.93 (2H, d, J=9 Hz), 10.63 (1H, brs)

Elemental analysis Calcd. for C$_{17}$H$_{14}$N$_2$O$_5$S: C, 56.97; H, 3.94; N, 7.82: Found: C, 57.01; H, 3.90; N, 7.95.

What we claim is:

1. A compound of the formula:

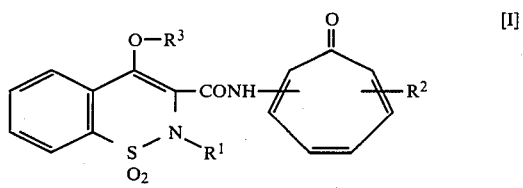

wherein

R$^1$ is hydrogen or lower alkyl,

R$^2$ is hydrogen, hydroxy, halogen, lower alkyl or lower alkoxy, and

R$^3$ is hydrogen or phenyl (lower) alkenoyl, and pharmaceutically acceptable salts thereof.

2. A compound of claim 1, wherein R$^3$ is hydrogen.

3. A compound of claim 2, wherein R$^1$ is lower alkyl.

4. A compound of claim 3, wherein R$^1$ is methyl.

5. A compound of claim 4, wherein R$^2$ is hydrogen.

6. A compound of claim 5, which is 4-hydroxy-2-methyl-N-(1-oxo-2,4,6-cycloheptatrien-2-yl)-2H-1,2-benzothiazine-3-carboxamide 1,1-dioxide.

7. A compound of claim 1, wherein R$^3$ is phenyl (lower) alkenoyl.

8. A compound of claim 7, which is N-(1-oxo-2,4,6-cycloheptatrien-2-yl)-2-methyl-4-cinnamoyloxy-2H-1,2-benzothiazine-3-carboxamide 1,1-dioxide.

9. A pharmaceutical anti-inflammatory composition comprising an anti-inflammatory effective amount of a compound of claim 1, in association with a pharmaceutically acceptable, substantially nontoxic carrier or excipient.

10. A method for treatment of inflammation, which comprises administering an anti-inflammatory effective amount of a compound of claim 1 to a human being or an animal.

* * * * *